(12) United States Patent
Herold et al.

(10) Patent No.: US 6,350,788 B1
(45) Date of Patent: Feb. 26, 2002

(54) LOW-FOAM SURFACTANT CONCENTRATES FOR USE IN THE DOMAIN OF PLANT GROWTH STIMULATION

(75) Inventors: Claus-Peter Herold, Mettmann; Stephan Von Tapavicza, Erkrath; Heinz Mueller, Monheim; Heinz Boettcher, Erkrath, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/341,731

(22) PCT Filed: Jan. 7, 1998

(86) PCT No.: PCT/EP98/00052

§ 371 Date: Oct. 22, 1999

§ 102(e) Date: Oct. 22, 1999

(87) PCT Pub. No.: WO98/31222

PCT Pub. Date: Jul. 23, 1998

(30) Foreign Application Priority Data

Jan. 15, 1997 (DE) .......................................... 197 01 127

(51) Int. Cl.$^7$ ...................... B01F 17/56; B01D 12/00; C09K 17/00

(52) U.S. Cl. ................................. 516/204; 516/DIG. 6; 504/362; 47/58.1; 71/64.1; 71/903; 510/470

(58) Field of Search ............................ 516/204, DIG. 6; 504/362, 363; 47/58.1, DIG. 10; 71/903, 64.1; 510/470

(56) References Cited

U.S. PATENT DOCUMENTS

| | | | | |
|---|---|---|---|---|
| 2,867,944 A | * | 1/1959 | Fletcher | 47/58.1 |
| 5,306,442 A | * | 4/1994 | Hill et al. | 516/132 |
| 5,308,531 A | * | 5/1994 | Urfer et al. | 510/470 |
| 5,366,532 A | * | 11/1994 | Fages et al. | 71/64.07 |
| 5,385,750 A | * | 1/1995 | Aleksejczyk et al. | 510/470 |
| 5,624,843 A | * | 4/1997 | Varadaraj et al. | 435/262.5 |
| 5,670,471 A | * | 9/1997 | Amalric et al. | 510/470 |
| 5,677,273 A | * | 10/1997 | Schmid et al. | 510/506 |
| 5,696,074 A | * | 12/1997 | Nickel et al. | 510/470 |
| 5,698,441 A | * | 12/1997 | Varadaraj | 435/262.5 |
| 5,707,957 A | * | 1/1998 | Yianakopoulos et al. | 510/470 |
| 5,770,639 A | | 6/1998 | Ritter et al. | 523/132 |
| 5,795,978 A | * | 8/1998 | Ansmann et al. | 510/470 |
| 5,888,934 A | * | 3/1999 | Townson et al. | 504/206 |
| 5,928,993 A | * | 7/1999 | Johansson | 516/204 |
| 6,122,860 A | * | 9/2000 | Von Tapavicza et al. | 47/58.1 |

FOREIGN PATENT DOCUMENTS

| | | |
|---|---|---|
| DE | 44 28 269 | 2/1996 |
| DE | 195 48 314 | 6/1997 |
| WO | WO93/22917 | 1/1993 |

OTHER PUBLICATIONS

Rompp Chemielexikon, Band 4, 9. (1991) month unknown, pg.3451.

* cited by examiner

*Primary Examiner*—Daniel S. Metzmaier
(74) *Attorney, Agent, or Firm*—John E. Drach; Steven J. Trzaska

(57) ABSTRACT

A low-foam wetting composition which, when mixed with water, enhances the penetration and spread of water on a plant, the composition containing: (a) an alkyl polyglycoside corresponding to formula I $$R-O-(G)_x \qquad (I)$$

wherein R is a primary hydrocarbon radical having from 8 to 18 carbon atoms, G is a glycose unit having 5 or 6 carbon atoms, and x is a number from 1 to 10; (b) an olefinically unsaturated alcohol; and (c) a lower water-soluble alcohol.

16 Claims, No Drawings

LOW-FOAM SURFACTANT CONCENTRATES FOR USE IN THE DOMAIN OF PLANT GROWTH STIMULATION

BACKGROUND OF THE INVENTION

It is known that the apparently simple measure of watering areas of ground covered in particular by dense plant growth can present considerable difficulties. A typical example of this are regularly maintained grassed areas which are subjected locally to pedestrian and/or vehicular traffic. For example, it is known from the maintenance of golf courses or other comparable sports fields and recreation grounds that relatively small or even relatively large areas of grass can dry out despite regular watering. When such areas are watered, the water does not penetrate deeply into the soil and, above all, does not penetrate to the roots of the grass. This can be attributed on the one hand to so-called thatch which, even on the surface of the ground, diverts rainwater from the roots so that the corresponding areas of grass become undernourished, shallow-rooted and unhealthy through overdrying.

However, even uniform distribution of the water on reaching the surface of the ground can present difficulties. Homogeneous spreading of the water applied, especially into the particular root zone, often does not occur. Instead, the water applied trickles in narrow streams into deeper layers of soil so that the damage mentioned above can be caused there also. Additional difficulties can arise where soil has been compacted which is unavoidable in areas subjected to pedestrian and/or vehicular traffic. The problems mentioned not only concern the process of watering. Understandably, corresponding difficulties attend the introduction of nutrients and/or protection agents in uniform distribution into the root zone.

It is known that the problems mentioned above can be better managed by adding wetting agents to the water and/or aqueous treatment formulations used for watering in order to reduce the surface tension of the water in known manner and, in this way, to ensure better spreading of the aqueous phase throughout the soil and particularly in the root zone. Practical use is made of this in the maintenance of sports fields and golf courses and in the protection of other green areas.

The problem addressed by the present invention was to homogenize, intensify and control the introduction of water into—above all—densely covered areas of ground using a certain wetting aid with the character of an o/w surfactant. More particularly, the teaching according to the invention seeks in particular to provide corresponding low-foam wetting aids in the form of highly concentrated water-containing concentrates which, for practical application, may simply be mixed with the water used for watering.

BRIEF SUMMARY OF THE INVENTION

In a first embodiment, therefore, the present invention relates to a low-foam wetting aid in the form of a highly concentrated but free-flowing and pourable water-containing surfactant-based concentrate for intensifying the penetration and spreading of water around the roots of plants during watering. The water-containing concentrates according to the invention contain alkyl(poly)glycoside compounds of the o/w type—hereinafter also referred to as "APG" compounds—as an ecologically safe surfactant component. Together with these surfactant components of the APG type, the water-containing concentrate according to the invention contains olefinically unsaturated alcohols, optionally in admixture with partial esters of fatty acids with polyhydric alcohols, as foam suppressors/defoamers and, finally, lower water-soluble alcohols as viscosity controllers.

DETAILED DESCRIPTION OF THE INVENTION

A first important defining element for the teaching according to the invention lies in the choice of compounds belonging to a certain class as wetting aids with the character of o/w surfactants. The class of compounds in question are alkyl (poly)glycosides (APG components or compounds) which per se are already widely used in a totally different technical field. APG compounds are used as surfactants in detergents, including laundry detergents. A number of factors are important to their use on an industrial scale. It is known that APG-based wetting agents can be based entirely on natural materials. They are obtained as products of the reaction of fatty alcohols with glucose, oligoglucoses or even—with a simultaneous reduction in chain length—with polyglycosides, such as starch, with the general formula $$R\text{---}O\text{---}(G)_x,$$

in which R is a primary, preferably linear aliphatic hydrocarbon radical containing in particular 8 to 18 carbon atoms and G is a glycose unit containing 5 or 6 carbon atoms, preferably glucose. In the class of surfactants in question, the degree of oligomerization x, which indicates the distribution of monoglycosides and oligoglycosides, normally assumes a value of 1 to 10 and may be, for example, a number of about 1.2 to 4 and is preferably a number of about 1.2 to 2. Reference may be made to the extensive expert knowledge and literature available on the production and properties of APG compounds.

In their earlier German patent application DE 195 48 314, applicants describe a modified process for stabilizing soil threatened by erosion in which—to intensify surface stabilization—impregnation of the soil is carried out in several stages, an aqueous formulation containing biologically safe wetting agents to accelerate and/or intensify wetting of the soil with aqueous phase being used in the first stage. Preferred wetting agents are nonionic wetting aids with HLB values of at least 7, preferably 8 or higher and more preferably in the range from 10 to 18. A particularly suitable class of biologically safe wetting agents of this type are the APG compounds with which the teaching of the present invention is also concerned. In the course of the work culminating in the earlier patent application mentioned above, it was found that APG-based wetting aids are not only particularly effective in the field of soil stabilization, their use also promotes the development and protection of existing plant growth to an unexpectedly high level.

On the basis of this discovery, another problem addressed by the present invention was to provide a formulation of the APG-based wetting aid which would satisfy all the various practical requirements. Without any claim to completeness, the following observations are relevant in this regard:

The high foaming capacity of the APG-based nonionic wetting aid demanded by the consumer for use in detergents is not only undesirable for the application with which the present invention is concerned, it can represent a major disadvantage. So-called foam suppressors of various kinds are known in the field of detergents; however, the additional problem arose for the application according to the invention of finding or rather selecting a defoamer which would be totally blolotially gafa and which would not impede and, preferably, would even promote plant growth. At the same time, the combination of active agents according to the invention would lend itself to formulation as a readily water-dilutable concentrate which, in turn, would adequately lend itself to portioning, even at normal temperatures.

The teaching according to the invention is based on the observation that selected alcohols of the type defined hereinafter can be effective foam suppressors where surface-active APG compounds are used. However, the mixing of water-based APG concentrates with the alcohol-based foam suppressors/defoamers results in the formation of thickened non-flowable gels. Then, in the development of the teaching according to the invention, it was found that the addition of limited quantities of lower monohydric alcohols and, in particular, the addition of limited quantities of ethanol to the APG/fatty alcohol concentrate reestablishes and guarantees flowability and pourability, even at room temperature.

In a first embodiment, therefore, the teaching according to the invention relates to the described concentrates of the three useful materials or rather auxiliaries: APG-based wetting component of the o/w type, foam suppressor/defoamer based on olefinically unsaturated alcohols and lower water-soluble alcohols as viscosity controllers. These three components and their preferred quantity ranges are discussed in detail in the following.

Preferred APG components contain alkyl groups based on at least substantially saturated so-called head-fractionated fatty alcohols, i.e. based on fatty alcohols containing 8 to 14 and, more particularly, 8 to 12 carbon atoms. Particularly preferred APG components for the use according to the invention are reaction products of $C_{8/10}$ fatty alcohols and glucose, oligoglucoses and/or polyglycoses. The so-called DP value (average degree of polymerization or degree of oligomerization x in the above formula) is again in the range from 1 to 10, preferably in the range from 1 to 5 and more preferably in the range from about 1.2 to 4.

The quantities of APG component (determined as water-free active substance) used in the wetting aid concentrates according to the invention are normally at least 15% by weight and preferably at least 20% by weight. In the context of this definition, the upper limit to the APG content is about 35 to 40% by weight, APG contents (water-free active substance) of about 25 to 30% by weight being particularly preferred.

Suitable foam suppressors/defoamers are olefinically unsaturated alcohols containing preferably 4 to 28 and, more preferably, 8 to 28 carbon atoms. Olefinically unsaturated $C_{12-24}$ fatty alcohols are particularly suitable, special significance being attributed to corresponding fatty alcohols of natural origin. Within this class, fatty alcohols or fatty alcohol mixtures with a high proportion of olefinic double bonds which may be assigned at least predominantly to the $C_{16/18}$ fatty alcohols are particularly preferred mixing components. It is known that the number of olefinic double bonds in the fatty alcohol molecule determines the solidification range of the particular useful material. According to the invention, corresponding fatty alcohols or fatty alcohol mixtures with solidification ranges below 20 to 25° C. and more particularly in the range from, or below, 10 to 15° C. are preferred.

In one advantageous embodiment, the above-mentioned fatty alcohols are used in admixture with partial esters of saturated and, in particular, at least partly olefinically unsaturated fatty acids with polyhydric alcohols containing 2 to 6 carbon atoms and, more particularly, 3 to 5 carbon atoms as foam suppressor side foamers. Thus, glycerol partial esters of natural fatty acids in particular can be important components for mixing with corresponding fatty alcohols, substantially equal amounts of fatty alcohol and fatty acid partial ester or corresponding mixtures with several times the amount of partial ester, based on the fatty alcohol, being preferred mixtures. A particularly preferred mixing component is glycerol monooleate. Suitable mixing ratios of fatty alcohol to fatty acid partial glyceride are, for example, in tho range from about 1:1 to 1:10, preferably in the range from 1:1 to 1:5 and more preferably in the range from about 1:1 to 1:3 parts by weight.

In addition to the unsaturated fatty alcohols described above, olefinically unsaturated terpene alcohols are also suitable as foam suppressors/defoamers. The terpene alcohols are acyclic or mono-, bi- or tricyclic, polyolefinically unsaturated alcohols of vegetable origin containing between 10 and 40 carbon atoms. The terpene alcohols are preferably used in the form of their naturally occurring mixtures as foam suppressors/defoamers. Pine oil—a mixture of various terpineols, such as α- and β-terpineol, α-fenchyl alcohol, borneol and isoborneol, as described in Römpp's Chemielexikon, page 3451, Vol. 4, 9th Edition, 1991—is particularly preferred. Pine oil also contains small quantities of other non-alcoholic compounds, for example camphor, anethol or estragol. Pine oil is obtained from resin-containing stumps and the root wood of various pine species by extraction with gasoline or chloroform and subsequent fractional distillation.

The defoamer component is normally present in smaller quantities—based on active substance—than the APG component. Mixtures in which the defoamer is used in far smaller amounts are preferred. Thus, multicomponent concentrates of which the defoamer content is in the range from about 10 to 25% by weight are preferred, those with defoamer contents of about 15 to 20% by weight being particularly preferred.

The lower water-soluble monohydric alcohols used as viscosity controllers are, in particular, corresponding $C_{1-4}$ compounds, ethanol being the most important viscosity controller. The quantity in which the viscosity controller is used is determined by the type and quantity of the two above-mentioned components and by the total amount of water present in the multicomponent mixture. Compositions—preferably based on ethanol—of at least about 5 to 7% by weight as the lower limit and 12 to 25% by weight as the upper limit are particularly suitable for the viscosity controller. Quantities of ethanol of about 5 to 20% by weight generally influence viscosity sufficiently to achieve the flowability and pourability of the multicomponent mixture, even at room temperature, required in accordance with the invention.

The water content of the multicomponent concentrates according to the invention is generally at most about 50% by weight. In preferred embodiments, however, it is lower. Thus, ranges of from about 30 to 45% by weight are suitable for the water content of the multicomponent mixture, the range from about 35 to 40% by weight being particularly suitable.

The wetting aid concentrates according to the invention are capable of initiating the desired effects of uniform wetting of plant material with the aqueous phase throughout the root zone even when added in very small quantities of, for example, 0.1% by weight, based on the total water used for watering. The wetting aid concentrates defined in the foregoing are preferably added to the water used for watering in quantities of preferably 0.1 to 5% by weight and more preferably about 0.5 to 2% by weight, based on the total aqueous phase.

In another embodiment, the invention also makes use of the wetting aids to intensify the input of nutrients and/or protection agents, such as herbicides and/or fungicides, for promoting and protecting plant growth. These additional auxiliaries may be applied in known manner in the form of aqueous solutions, emulsions and/or dispersions using the described wetting aids according to the invention.

EXAMPLE

A mixture of the following components (% by weight, based on the total weight of the undiluted concentrate) is used as a low-foam surfactant concentrate in accordance with the teaching of the invention: ca. 45% by weight of the APG-based surfactant component, ca. 20% by weight of the highly unsaturated fatty alcohol, ca. 12% by weight of ethanol, balance water.

The APG compound used is the APG product marketed by Applicants under the name of "APG 220 UP" in which the alkyl group derives by far predominantly from a $C_{10}$ fatty alcohol of natural origin (active substance content ca. 65%). The fatty alcohol used as foam suppressor/defoamer is the product marketed by applicants under the name of "HD Ocenol 80/85". This product is an olefinically unsaturated fatty alcohol of natural origin by far predominantly in the $C_{16/18}$ range with a hydroxyl value of 205 to 215, an iodine value of 84 to 89 and a solidification range of 6 to 14° C.

This wetting aid is performance-tested as follows:

An area of grass with extensive dry patches was divided into two plots of substantially equal size with comparable damage patterns. The plots had the following dimensions:

test plot A: 25 m×16.5 m=412.5 m² test plot B: 24 m×17.5 m=420 m²

Throughout the duration of the test, both plots were adequately watered artificially in the same way according to the natural rainfall. Plot A was watered with no further additions to the artificially applied water. In the case of plot B, 250 ml of wetting aid per 100 m² were applied during watering at the beginning of the test.

A similar treatment of plot B was undertaken after 3 weeks and again after another 4 weeks.

Evaluation of the two plots after 10 weeks produced the following results:

Plot A—no change in the damage pattern, no change in the size of the dry patches.

Plot B—80% reduction in the size of the dry patches, good recovery of plant growth in the regenerated patches.

What is claimed is:

1. A low-foaming wetting concentrate composition for enhancing penetration and spread of water around roots of a plant during watering, the composition comprising:
   (a) from 15 to 40% by weight of an alkyl polyglycoside corresponding to formula I

   (I)

wherein R is a primary hydrocarbon radical having from 8 to 18 carbon atoms, G is a glycose unit having 5 or 6 carbon atoms, and x is a number from 1 to 10;
   (b) from 10 to 25% by weight of an olefinically unsaturated fatty alcohol; and
   (c) from 5 to 25% by weight of a lower water-soluble alcohol, and
   (d) water, all weights being based on the weight of the composition.

2. The composition of claim 1 wherein R is a primary hydrocarbon radical having from 8 to 14 carbon atoms.

3. The composition of claim 1 wherein the olefinically unsaturated alcohol is derived predominantly from $C_{12-24}$ fatty alcohols having a high proportion of olefinic double bonds and solidification ranges below 20° C.

4. The composition of claim 1 further comprising a fatty acid partial glyceride.

5. The composition of claim 4 wherein the fatty acid partial glyceride is glycerol monooleate.

6. The composition of claim 4 wherein the olefinically unsaturated alcohol and the fatty acid partial glyceride are present in the composition in a ratio by weight of from about 1:1 to about 1:10.

7. The composition of claim 1 wherein the lower water soluble alcohol is a lower monohydric alcohol having from 1 to 4 carbon atoms.

8. The composition of claim 1 wherein the composition has a water content of 50% by weight, or less, based on the weight of the composition.

9. A process for treating a plant comprising:
   (a) providing water;
   (b) providing a low-foaming wetting concentrate composition containing:
      (i) from 15 to 40% by weight of an alkyl polyglycoside corresponding to formula I

   (I)

wherein R is a primary hydrocarbon radical having from 8 to 18 carbon atoms, G is a glycose unit having 5 or 6 carbon atoms, and x is a number from 1 to 10,
      (ii) from 10 to 25% by weight of an olefinically unsaturated alcohol;
      (iii) from 5 to 25% by weight of a lower water-soluble alcohol, and
      (iv) water, all weights being based on the weight of the composition;
   (c) mixing (a) and (b) to form an aqueous composition; and
   (d) applying the aqueous composition onto the plant.

10. The process of claim 9 wherein the low-foam wetting composition is present in the aqueous composition in an amount of from 0.1 to 5% by weight, based on the weight of the aqueous composition.

11. The process of claim 9 wherein R is a primary hydrocarbon radical having from 8 to 14 carbon atoms.

12. The process of claim 9 wherein the olefinically unsaturated alcohol is derived predominantly from $C_{12-24}$ fatty alcohols having a high proportion of olefinic double bonds and solidification ranges below 20° C.

13. The process of claim 9 wherein the wetting composition further comprises a fatty acid partial glyceride, in admixture with the olefinically unsaturated alcohol, in a ratio by weight of from about 1:1 to about 1:10.

14. The process of claim 9 wherein the olefinically unsaturated alcohol is an olefinically unsaturated terpene alcohol.

15. The process of claim 9 wherein the lower water soluble alcohol is a lower monohydric alcohol having from 1 to 4 carbon atoms.

16. The process of claim 9 wherein the wetting composition has a water content of 50% by weight, or less based on the weight of the wetting composition.

* * * * *